United States Patent [19]

Martin et al.

[11] Patent Number: 4,616,642
[45] Date of Patent: Oct. 14, 1986

[54] SURGICAL DRAPE FOR CAESAREAN SECTION

[75] Inventors: Jeffrey A. Martin, Duluth; Philip S. Pomeroy, Marietta, both of Ga.

[73] Assignee: Kimberly-Clark Corporation, Neenah, Wis.

[21] Appl. No.: 647,289

[22] Filed: Sep. 4, 1984

[51] Int. Cl.$^4$ .......................... A61F 13/00
[52] U.S. Cl. .......................... 128/132 D
[58] Field of Search .......... 128/132 R, 132 D; 604/356, 357, 366, 368

[56] References Cited

U.S. PATENT DOCUMENTS

| Re. 26,759 | 1/1970 | Meiges | 128/132 |
|---|---|---|---|
| Re. 27,710 | 7/1973 | Melges | 128/132 D |
| 1,318,872 | 10/1919 | Hofstetter | 604/356 |
| 3,182,656 | 5/1965 | Pyne | 128/132 |
| 3,410,266 | 11/1968 | Krzewinski | 128/132 |
| 3,482,567 | 12/1969 | Franklin | 128/132 |
| 3,561,439 | 2/1971 | Bayer | 128/132 |
| 3,561,440 | 2/1971 | Bayer et al. | 128/132 |
| 3,654,047 | 4/1972 | Berkowitz | 161/7 |
| 3,668,050 | 6/1972 | Donnelly | 128/132 D |
| 3,669,106 | 6/1972 | Schrading et al. | 128/132 D |
| 3,721,234 | 3/1973 | Hadtke et al. | 128/132 D |
| 3,727,658 | 4/1973 | Eldridge | 150/52 R |
| 3,738,359 | 6/1973 | Lindquist et al. | 128/132 D |
| 3,856,006 | 12/1974 | Krzewinski | 128/132 |
| 3,881,474 | 5/1975 | Krzewinski | 128/132 D |
| 3,882,859 | 5/1975 | Ericson | 128/132 D |
| 3,930,497 | 1/1976 | Krebs et al. | 128/132 D |
| 3,934,587 | 1/1976 | Gordon | 128/284 |
| 4,040,418 | 8/1977 | Collins | 128/132 D |
| 4,089,331 | 5/1978 | Hartigan et al. | 128/132 D |
| 4,414,968 | 11/1983 | Amin | 128/132 D |

OTHER PUBLICATIONS

Walter, Carl W., "The Aseptic Treatment of Wounds", Macmillan Co., New York, 1948; p. 106, relied upon.

Primary Examiner—F. Barry Shay
Attorney, Agent, or Firm—William D. Herrick

[57] ABSTRACT

A surgical drape is provided having a flexible, nonwoven base sheet with a primary operative area, a flexible, liquid-impervious plastic film overlying and secured to one surface of the base sheet in at least a portion of the primary operative area, a sheet of first liquid-absorbent material secured to the outer surface of the liquid-impervious plastic film in at least a portion of the primary operative area, the primary operative area having a region in which the base sheet, the liquid-impervious plastic film and the first liquid-absorbent material are coextensive, the coextensive region having a fenestration, and a U-shaped region of a second liquid-absorbent material located in the primary operative area, partially surrounding and spaced from the fenestration.

15 Claims, 4 Drawing Figures

SURGICAL DRAPE FOR CAESAREAN SECTION

TECHNICAL FIELD

The present invention relates generally to surgical drapes and, more particularly, to an improved construction for the operative areas of surgical drapes, such as the fenestration and operative fields of Caesarean section drapes.

BACKGROUND ART

Surgical gowns and drapes are routinely used in surgical, obstetrical and like procedures. Such drapes at least partially cover the patient and have a surgical access opening or fenestration located generally in a central portion of the drape which exposes only that part of the anatomy on which the procedure is being performed. The surgical drape provides protection from contamination to the surgical area and also protects the personnel involved in the surgical procedure.

Although surgical drapes have in the past been made from cloth, such as linen, muslin and other similar woven fabrics, their initial cost and the subsequent costs associated with their laundering and the difficulties concomitant with laundering and sterilization have resulted in a trend toward replacment with disposable-type drapes. It also has been recognized that nonwoven, particularly fluid-repellent materials, afford the best protection from strike-through and potential contamination which results therefrom.

In U.S. Pat. No. 3,668,050 there is described an improved disposable surgical drape which combines a fibrous sheet having a primary operative area, a fluid-impervious flexible plastic layer laminated to the base sheet in the primary operative area, and a sheet of fluid-absorbent flexible plastic foam material on the outer surface of the film. Although such a drape is suitable for many surgical applications, particularly laparotomies, it is preferred in other types of procedures to employ a drape with specific properties required by that procedure. Thus, in those procedures in which large volumes of bodily fluids are generated, provisions for draining or absorbing excess fluids are required. In some instances, it is desirable to provide a drape with a fenestration of a particular configuration which conforms to a portion of the anatomy being operated upon. In some procedures it is also desirable to provide a means for adhering the surgical drape in the region of the fenestration to the patient in order to prevent movement of the drape during the operation or flow of bodily fluids from between the surgical drape and the patient. Thus, a surgical drape suitable for one application will not necessarily be suitable for other surgical or related applications. To be effective in a particular procedure, the drape should be of such structure and material to overcome each difficulty which arises.

DISCLOSURE OF INVENTION

The present invention is directed to a surgical drape having a fenestration which is suitable for use in high fluid procedures and, in particular, in Caesarean sections. This drape, in addition to a composite structure having a liquid-impervious plastic film and a superposed first liquid-absorbent material located on a base sheet in the operative field surrounding the fenestration, also includes a U-shaped region having a supplemental or second absorbent material arranged partially surrounding the fenestration which aids in controlling run-off and in absorbing large volumes of bodily fluids released during the surgical procedure, such as, in the case of a Caesarean section, amniotic fluid or fluids used during the procedure, such as irrigation fluids. The supplemental absorbency of this region also helps to eliminate reintroduction of fluids into the exposed surgical site, thereby reducing the risk of contamination. This region, which is positioned in the operative area to intercept such fluids where the flow of run-off is heaviest, is arranged at least partially surrounding and spaced from the fenestration on at least three sides and is retained, preferably, within a novel pocket the opening of which faces the fenestration.

When used for Caesarean section procedures, the fenestration of the surgical drape of this invention is also preferably provided with an ovate-rotundate configuration, allowing access and conforming to the limited area of the anatomy in which surgery is performed.

BEST MODES FOR CARRYING OUT THE INVENTION

Figure 1:
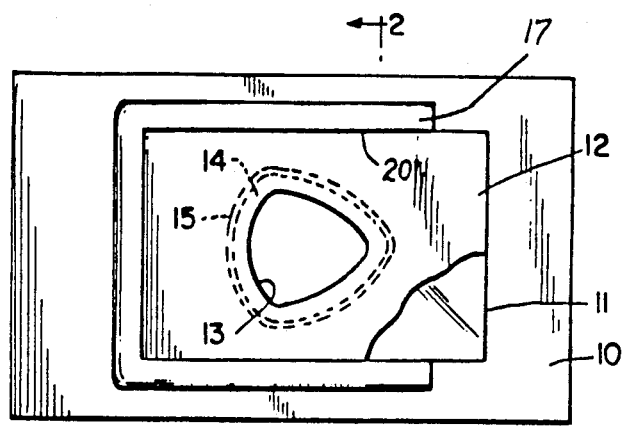
FIG. 1 is a plan view of a Caesarean drape embodying the present invention.

While the present invention is susceptible to various modifications and alternative forms, certain specific embodiments thereof are shown by way of example in the drawings which are described in detail herein. It should be understood, however, that the drawings and description provided herein are not intended to limit the invention to the particular forms disclosed but, on the contrary, the intention is to cover all modifications, equivalents and alternatives falling within the spirit and scope of the invention.

As illustrated in FIG. 1, the surgical drape of the present invention includes a base sheet 10, preferably formed from a substantially rectangular sheet of material which is resistant to the passage of liquids and, particularly, microorganisms. Preferably, the base sheet is formed from a material such as a spunbond/melt blown/spunbond material described in greater detail in U.S. Pat. No. 4,041,203, assigned to the assignee of the present invention and incorporated herein by reference. The material of the base sheet may also be treated to provide low surface tension liquid repellency with a suitable material, such as a fluorinated material as, for example, a fluorocarbon or the like. Preferred are aqueous latexes and particularly preferred is a weakly cationic aqueous latex containing 20 percent by weight of a linear copolymer of a perfluoroalkyl acrylate and a polyoxyalkylene acrylate.

A sheet of liquid- or fluid-impervious plastic film 11 is bonded to the top surface of the base sheet 10 in at least a portion of the primary operative field of the sheet. By the terms "operative area", "primary operative area" or "operative field" is meant that area or portion of the drape which covers the patient or extends slightly beyond the patient's body and which surrounds the fenestration, which fenestration is located at the site of surgery or like procedure. This is the area which is most likely to be contacted during a surgical procedure by bodily or irrigation fluids or the like. The dimensions of the operative area of the Caesarean drape of the present invention are preferably large enough not only to effectively reduce run-off and strike-through but also to allow placement of the infant after delivery. Accordingly, the operative field of the drape should extend laterally over the patient and preferably to the sides of the operating table and should also extend substantially both above and below the fenestration to provide the room necessary for placement of the infant after delivery.

The film 11 may be bonded or laminated to the base sheet 10 by any suitable means, such as by means of an adhesive or by extruding the film directly on the base sheet 10. The film 11 provides a liquid-impervious barrier on the top surface of the operative area of the sheet 10 surrounding the fenestration so that any liquids which contact this area cannot strike through the sheet. The film also prevents the transfer of bacteria through the sheet to insure sterile conditions in the operative area.

The film, like the base sheet, should be capable of remaining stable under the conditions commonly employed in treating a disposable drape to render it sterile.

Examples of suitable films include those materials formed from homopolymers and copolymers of monomers having ethylenic unsaturation, such as polyethylene (as, for example, 1.25-mil antistatic polyethylene film manufactured by Clopay Film Corporation), antitstatic polypropylene, copolymers of polyethylene and polypropylene, polyethylene methylacrylate copolymer film, and vinyl chloride films.

To remove some of the liquid generated during the procedure, there is provided in at least a portion of the operative area of the outer surface of the drape a sheet of a flexible liquid- or fluid-absorbent material 12, such as a plastic foam material, secured to the outer surface of the liquid-impervious film 11. The absorbent material 12 may be bonded to the film 11 by any suitable means, such as by use of an adhesive, by fusing, by laminating, or by extruding the film 11 directly on the material 12.

The absorbent nature of the flexible absorbent material 12 restricts fluid run-off and, because of the layer of liquid-impervious film 11 lying intermediate the absorbent material 12 and the base sheet 10, strike-through is prevented. The preferred material for the absorbent layer 12 is an open-cell foam, such as a polyurethane foam or the like.

Figure 3:
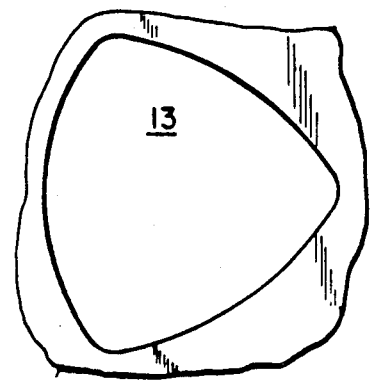
FIG. 3 is an enlarged plan view of the fenestration of the drape illustrated in FIG. 1.
Figure 4:
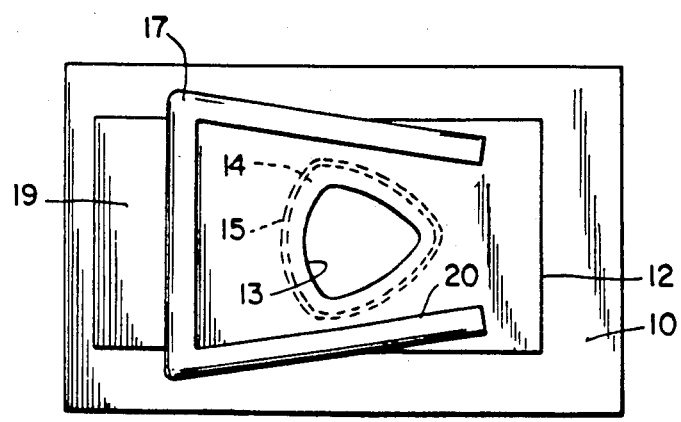
FIG. 4 is a plan view of another embodiment of the surgical drape.

To allow surgical access to the relevant anatomical site of the patient, a portion of the operative field, particularly where the base sheet, liquid-impervious film and first absorbent material layer are coextensive, has a fenestration. For use in Caesarean section surgical procedures, the surgical drape of the present invention is provided with a "tear-drop" for ovate-rotundate fenestration 13, as illustrated in FIGS. 1, 3 and 4. This particular configuration provides the ideal fenestration for conformability to the delivering mother's abdomen, for the surgical incision, for the subsequent delivery and to retain fluids on the drape so that the fluids do not run under the sheet and contaminate the patient. Suitable dimensions for the fenestration are about 7 to about 10 inches across the widest part of the base and between the most widely separated points, top to bottom, respectively. Preferably, the fenestration is placed symmetrically on the centerline of the drape, which centerline extends from the top to the bottom of the drape, thereby dividing the drape into two equal halves and the fenestration into two mirror-image portions. An imaginary horizontal straight line extending across the fenestration between the two horizontally most widely separated points on the sides of the fenestration and lying perpendicular to the centerline of the fenestration (and also the centerline of the drape when the two coincide) divides the fenestration into two asymmetrical portions. The ratio of the portion of the centerline lying above the imaginary line to that lying below the line is preferably about 3:1.

An adhesive layer, preferably in the form of a pressure sensitive adhesive 14, is provided on base sheet 10 to assist in retaining the surgical drape in the appropriate anatomical location during the course of the delivery and, in conjunction with the conformability to the mother's adbomen provided by the o-vate-rotundate configuration, to reduce flow of fluids between the drape and the mother3 s abdomen in a region adjacent and surrounding the fenestration. A release liner 15, preferably a one-piece release liner, is positioned substantially coextensive with the region of pressure sensitive adhesive and may be removed immediately prior to placement of the drape on the patient.

Spaced from and surrounding the fenestration 13 on at least three sides is a region having a second or supplemental absorbent material 16. This supplemental region is provided to prevent run-off and retain excess liquids generated in high fluid procedures, such as Caesarean section operations, which would ordinarily exceed the capacity of the layer of flexible, first liquid-absorbent material 12 provided in the operative field. The preferred configuration of this supplemental absorbent region is a U-shape with the two limbs arranged laterally, or on either side, of the fenestration. As shown in FIG. 1, the limbs may be arranged approximately parallel to one another, joining the base portion of the region of second absorbent material below the fenestration. However, alternatively and preferably, the limbs of the U-shaped supplemental region are disposed so that they are closer to one another at the upper or open part of the "U" than at the bottom where they join the base, as illustrated in FIG. 4.

Figure 2:
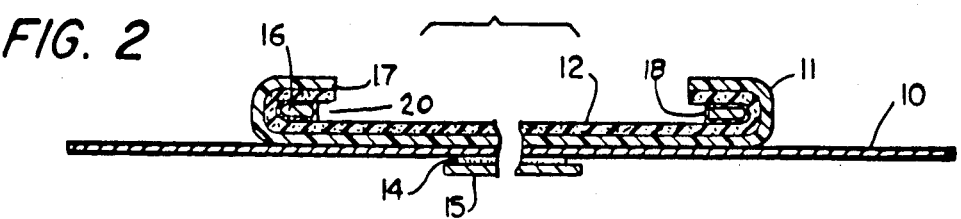
FIG. 2 is a section taken along line 2—2 of FIG. 1.

The absorbent material forming this second absorbent region 16 may be adhered or otherwise bonded to the base sheet or the plastic film but is preferably bonded to the flexible absorbent material 12. However it is preferably contained within a pouch or pocket 17 spaced from and surrounding the fenestration and located, preferably, at or near the periphery of the operative field. The overall shape and orientation of the pocket 17 and supplemental region 16 are commensurate to one another. This pocket may be formed and suitably bonded as a separate member to the base sheet 10, impervious film 11, or flexible absorbent layer 12. It preferably has an outer surface or layer formed from a liquid-impervious material such as that used to form film layer 11. It may also have an inner absorbent layer formed from a material such as that used for absorbent layer 12. Preferably the material which defines pocket 17 is formed from a laminate of the preferred materials which form layers 11 and 12. In a preferred embodiment, such as that shown in FIGS. 1, and 4, and particularly FIG. 2, this pocket is formed from the edge portions of the laminate of the impervious layer 11 and absorbent material 12 which is folded back upon itself toward the fenestration so as to define the pocket, which has one or more openings or slots 20 facing the fenestration. The edge of the opening 20 may be bonded to the surface below it to form a plurality of openings, thereby more securely confining the second absorbent material within the pocket 17 while still allowing access by liquids to the absorbent material.

In a Caesarean section drape according to the present invention, it may be desirable to have an area on the drape on which to place the infant after delivery to clamp and cut the umbilical cord. Since the type of absorbent material preferred for layer 12, polyurethane, is both liquid absorbing and has a high coefficient of friction, such a layer provides a suitable surface; however, other similar materials providing these properties may also be used. A sufficient area may be allocated for such a purpose by providing additional space, preferably either above the fenestration or, alternatively, as shown in FIG. 4, an appropriate place may be provided on a portion 19 of absorbent layer 12 extending below the base of the U-shaped supplemental region. This may be accomplished by bonding the base of the U-shaped absorbent region 16 or the base of a separate pocket containing the supplemental absorbent material to an elongated sheet of absorbent material or film laminate thereof or by using a second sheet of film/absorbent laminate intermediate the base sheet and the film/absorbent layer (11/12) and extending below the pocket formed from the edge thereof.

The material used as the supplemental region of absorbent material 16 may be of any composition and dimensions suitable to absorb large volumes of bodily fluids. Preferred materials include cellulosic materials in various forms and combinations, such as ground or pulverized wood pulp, cellulose wadding, webs or matrices of a cellulosic material, such as wood fibers; at least one of the foregoing and a thermoplastic material, for example, a polyolefin, such as polyethylene, or the like; staple fibers, such as rayon or cotton, either loose or in web form; superabsorbent materials (SAMs) and the like and combinations of the foregoing.

Among the preferred absorbent materials used as the second absorbent material surrounding the fenestration, either alone or in combination with a SAM, is a mixture of polypropylene and cellulose, which is mixed and heated to form a coformed blend. The cellulose is generally present in the form of wood fibers and the resulting product is obtained as an airformed web. The range of composition of this polypropylene/cellulose coformed absorbent material is, by weight, based on the total weight of the composition, 50 percent wood pulp/50 percent polypropylene to 80 percent wood pulp/20 percent polypropylene, preferably 70 percent wood pulp/30 percent polypropylene. The preferred polypropylene/cellulosic melt blown fiber blend of 70 percent wood pulp and 30 percent polypropylene has a basis weight of 190 grams per square meter.

It is preferred that the second absorbent material contain about 1 to about 30 percent, preferably about 3 to about 10 percent, by weight, based on the total weight of the supplemental absorbent material, of superabsorbent material since SAMs are capable of absorbing many time their own weight of water or aqueous fluids and thereby serve to greatly reduce the risk of infection due to reintroduction of fluids generated during the procedure to the surgical site. Suitable SAMs should be non-toxic, be capable of withstanding the temperatures used with chemical sterilants such as ethylene oxide and be chemically inert toward such sterilants. Typical materials suitable for use as the superabsorbent material of the present invention and methods for their synthesis are set forth in U.S. Pat. Nos. 3,670,731, 3,669,103, 3,980,663, 3,983,095, 3,993,616, 4,192,727, 3,997,484, 3,628,534, and 4,155,880, the disclosures of which are incorporated herein by reference. Preferred SAMs include acrylates, polyacrylates, salts of polyacrylates, and grafts and copolymers of starch, cellulose and cellulose derivatives, such as carboxymethyl cellulose. The most preferred superabsorbent material is a sodium salt of a crosslinked polyacrylate. These superabsorbent materials may be used in a variety of solid forms including fiber, thin film or cellular structure. However, they are preferably used in particulate form, such as flakes, granules or as a powder, either alone or in combination with one or more of the foregoing listed absorbent materials.

When the absorbent material 16 which forms the supplemental region either contained within the excess fluid-retaining pocket 17 or existing independently is susceptible to migration, that is, is formed from particulate matter such as short fibers, flakes, granules, a powder, or the like, the fluid-retaining or absorbent material is preferably confined or retained within an external layer of a porous material 18 which defines an enclosure within which the absorbent material is retained or confined. The wrapping material should allow entry of liquid to the enclosure and the fluid-retaining material confined therein. A tissue or, preferably, a nonwoven spun bond material of a type similar to that which is used to make the spun bond/melt blown/spun bond laminate of the base sheet may be used.

INDUSTRIAL APPLICABILITY

The present invention finds utility as a surgical drape in those procedures, particularly surgical, where large volumes of liquid are generated during the procedure. The present invention has particular utility in Caesarean section procedures.

We claim:
1. A surgical drape comprising:
    a flexible, nonwoven base sheet having a primary operative area;
    a flexible, liquid-imprevious plastic film overlying and secured to one surface of said base sheet in at least a portion of said primary operative area; and
    a sheet of first liquid-absorbent material secured to the outer surface of said liquid-imprevious plastic film in at least a portion of said primary operative area, said primary operative area having a region in which said base sheet, said liquid-imprevious plastic film and said first liquid-absorbent material are conextensive, said conextensive region having a fenestration; and
    a second liquid-absorbent material located in said primary operative area and having a U-shaped region partially surrounding and spaced from said fenestration, said second liquid-absorbent material having its U-shaped region located within a U-shaped pocket commensurate thereto in shape, said pocket having an opening facing said fenestration and being defined by peripheral edge portions of a laminate of flexible, liquid-imprevious plastic film and liquid-absorbent material.

2. The surgical drape of claim 1 wherein said fenestration has an ovate-rotundate configuration.

3. The surgical drape of claim 2 wherein an imaginary straight line extending horizontally across the fenestration between the two horizontally most widely spaced points on the fenestration intersects the centerline of the fenestration and divides the fenestration into two asymmetrical portions.

4. The surgical drape of claim 3 wherein the ratio of the portion above to that portion lying below the horizontal line is about 3:1.

5. The surgical drape of claim 1 wherein said U-shaped region of second liquid-absorbent material is secured to at least one of said base sheet, said liquid-imprevious plastic film overlying said base sheet and said sheet of first liquid-absorbent material.

6. The surgical drape of claim 1 wherein said second absorbent material includes a superabsorbent material.

7. The surgical drape of claim 1 wherein the undersurface of said base sheet has a coating of pressure sensitive adhesive adjacent at least a portion of said fenestration.

8. The surgical drape of claim 7 wherein said pressure sensitive adhesive is provided with at least one removable peel strip covering said adhesive coating.

9. The surgical drape of claim 1 wherein said base sheet is liquid-repellent.

10. The surgical drape of claim 1 wherein said first liquid-absorbent material is a flexible foam material.

11. The surgical drape of claim 10 wherein said flexible foam material is a polyurethane.

12. The surgical drape of claim 1 wherein said second absorbent material contains a cellulosic material.

13. The surgical drape of claim 1 wherein said second absorbent material is confined, within an enclosure formed from a porous material.

14. The surgical drape of claim 1 wherein said U-shaped region of said second absorbent material is defined by two spaced apart limbs whose lower ends join the ends of a horizontally disposed base, said limbs being arranged with their upper ends being closer to one another than their lower ends.

15. A surgical drape comprising:
a flexible, nonwoven base sheet having a primary operative area;
a flexible, liquid-imprevious plastic film overlying and secured to one surface of said base sheet in at least a portion of said primary operative area;
a sheet of a first liquid-absorbent, flexible foam material secured to the outer surface of said liquid-imprevious plastic film in at least a portion of said primary operative area, said primary operative area having a region in which said base sheet, said liquid-imprevious plastic film and said first liquid-absorbent foam material are coextensive, said coextensive region having an ovate-rotundate fenestration in which an imaginary straight line extending horizontally across the fenestration between the two most horizontally widely spaced points on the fenestration intersect the centerline of the fenestration and the ratio of that portion of the centerline lying above to that portion lying below the horizontal line is about 3:1; and
a U-shaped region of said primary area being occupied by a second liquid-absorbent material confined within an enclosure formed from a porous material, which enclosure is retained within a U-shaped pocket commensurate in shape to said U-shaped region, said U-shaped pocket arranged partially surrounding and spaced from said fenestration with at least one opening in said pocket facing said fenestration and said pocket being defined by peripheral edge portions of a laminate of said flexible, liquid-imprevious plastic film and said sheet of first liquid-absorbent flexible form material.

* * * * *